United States Patent
Stagg et al.

(10) Patent No.: US 8,563,473 B2
(45) Date of Patent: *Oct. 22, 2013

(54) AQUEOUS HERBICIDAL CONCENTRATES OF AUXINIC CARBOXYLIC ACIDS WITH REDUCED EYE IRRITANCY

(75) Inventors: Nicola Stagg, Zionsville, IN (US); T. Craig Blewett, Zionsville, IN (US); Holger Tank, Zionsville, IN (US); Mei Li, Westfield, IN (US); Lei Liu, Carmel, IN (US)

(73) Assignee: Dow AgroSciences, LLC., Indianapolis, IN (US)

( * ) Notice: Subject to any disclaimer, the term of this patent is extended or adjusted under 35 U.S.C. 154(b) by 73 days.

This patent is subject to a terminal disclaimer.

(21) Appl. No.: 13/089,336

(22) Filed: Apr. 19, 2011

(65) Prior Publication Data

US 2011/0257012 A1  Oct. 20, 2011

Related U.S. Application Data

(60) Provisional application No. 61/325,939, filed on Apr. 20, 2010.

(51) Int. Cl.
*A01N 57/00* (2006.01)
*A01N 43/40* (2006.01)
*A01N 37/00* (2006.01)

(52) U.S. Cl.
USPC ........... 504/127; 504/128; 504/244; 504/254; 504/255; 504/260; 504/307

(58) Field of Classification Search
None
See application file for complete search history.

(56) References Cited

U.S. PATENT DOCUMENTS

| 5,118,444 A | 6/1992 | Nguyen |
| 2008/0207453 A1* | 8/2008 | Kramer et al. ................ 504/130 |

FOREIGN PATENT DOCUMENTS

| GB | 2 018 776 A | 10/1979 |
| WO | WO 2008/106107 A1 | 9/2008 |
| WO | WO2008106107 A1 | 9/2008 |

OTHER PUBLICATIONS

International Search Report and Written Opinion in PCT/US2011/032940 issued Oct. 6, 2011.

* cited by examiner

*Primary Examiner* — Alton Pryor
(74) *Attorney, Agent, or Firm* — Michael R. Asam

(57) ABSTRACT

Aqueous concentrates of choline salts of herbicidal auxinic carboxylic acids are less irritating to eyes than the commonly used aqueous concentrates of ammonium salts of herbicidal auxinic carboxylic acids.

7 Claims, No Drawings

AQUEOUS HERBICIDAL CONCENTRATES OF AUXINIC CARBOXYLIC ACIDS WITH REDUCED EYE IRRITANCY

CROSS REFERENCE TO RELATED APPLICATIONS

This application claims the benefit of U.S. Provisional Patent Application Ser. No. 61/325,939 filed Apr. 20, 2010.

FIELD OF THE INVENTION

This invention concerns the use of choline salts to reduce eye irritancy of aqueous herbicidal concentrates of commonly used ammonium salts of auxinic carboxylic acids derived from mono-, di- or trialkylamines.

BACKGROUND OF THE INVENTION

Aqueous concentrate formulations of pesticidal and plant growth modifying chemicals are widely used in agricultural, industrial, recreational and residential areas worldwide. The active ingredients of such concentrates are frequently carboxylic acids, more particularly their salts. An aqueous concentrate is essentially a solution of the active ingredient in water at relatively high concentration, intended for dilution in water prior to application by spraying or other means. Typically the aqueous concentrate is diluted with about 10 to about 100 times its own volume of water prior to application.

Many herbicidal carboxylic acids such as, for example, the phenoxycarboxylic acids like 2,4-D, 2,4-DB, MCPA, MCPB, mecopropand clomeprop, the benzoic acids like dicamba and chloramben, the picolinic acids like aminopyralid, picloram and clopyralid, the pyridinyloxyacetic acids like triclopyr and fluoroxypyr, and the quinolinecarboxylic acids like quinclorac and quinmerac are relatively insoluble in water in the acid form. Therefore, these herbicides are in many instances formulated as aqueous concentrates of water soluble salts. Commonly used salts of these herbicidal carboxylic acids used for preparing aqueous herbicide concentrates include, for example, ammonium, iso-propyl ammonium, dimethyl ammonium, triethyl ammonium, monoethanol ammonium, diethanol ammonium, triethanol ammonium, triisopropanol ammonium and the like, which are collectively referred herein as the ammonium salts.

The disadvantage of using ammonium salts of herbicidal carboxylic acids to prepare aqueous herbicide concentrates is that they can be irritating if accidentally splashed or otherwise injected into the eye of anyone handling such a formulation. This property may lead to restrictive labeling of the products that limits their usefulness in certain markets, even where the active ingredient itself provides no such hazard.

Choline is an essential nutrient for mammals, necessary for optimal health based on the Dietary Reference Intakes recommended by the National Academy of Sciences. Choline generally refers to the various quaternary ammonium salts containing the N,N,N-trimethylethanolammonium cation and a counterion $X^-$ such as, for example, chloride (choline chloride), hydroxide (choline hydroxide) or tartrate (choline tartrate).

Choline hydroxide can be mixed with 2,4-D in water and readily forms the choline salt of 2,4-D which has the structure

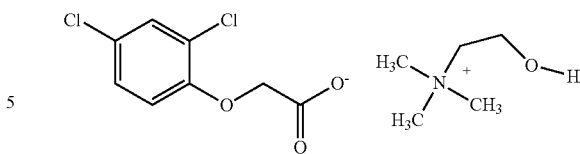

and readily forms a water soluble concentrate. This concentrate, when diluted in water and applied postemergently to susceptible plants, provides good weed control as disclosed in WO 2008/106107 A1.

It would be desirable to have an herbicidal carboxylic acid derivative that is at least as active as the commercially used carboxylic acid herbicide salts and highly soluble in water, but which is less irritating to eyes and therefore safer to use for those who handle and apply it.

SUMMARY OF INVENTION

It has now been surprisingly found that aqueous concentrates of choline salts of herbicidal auxinic carboxylic acids are less irritating to eyes than are the commonly used ammonium salts of such herbicidal auxinic carboxylic acids. These choline salts have herbicidal activity on an acid equivalent basis comparable to the commercially used carboxylic acid herbicide ammonium salts, such as iso-propyl ammonium, dimethyl ammonium, triethyl ammonium, monoethanol ammonium, diethanol ammonium, triethanol ammonium, triisopropanol ammonium salts and the like, but with reduced eye irritation. Furthermore, the choline salts can be conveniently formulated as aqueous concentrates.

The present invention concerns a method to reduce the eye irritancy of aqueous herbicidal concentrates of commonly used ammonium salts of auxinic carboxylic acids derived from mono-, di- or trialkylamines which comprises using the N,N,N-trimethylethanolammonium cation as the ammonium salt of the auxinic carboxylic acid.

Another aspect of the present invention concerns a mixture of one or more organophosphorous acid herbicide salts and the choline salts of the herbicidal auxinic carboxylic acids which provide an aqueous herbicide concentrate mixture of reduced eye irritancy.

Another aspect of the present invention concerns a method of improving the solubility in water of ammonium salts of auxinic herbicides which comprises using the N,N,N-trimethylethanolammonium cation as the ammonium salt of the auxinic herbicide.

DETAILED DESCRIPTION OF THE INVENTION

Herbicidal auxinic carboxylic acids are carboxylic acid herbicides with the same mode of action as indoleacetic acid and is meant to include benzoic acid herbicides such as chloramben, dicamba, 2,3,6-TBA and tricamba; pyridine carboxylic acid herbicides such as aminopyralid, clopyralid and picloram; pyridinyloxyacetic acid herbicides such as triclopyr and fluoroxypyr quinolinecarboxylic acid herbicides such as quinclorac and quinmerac; phenoxyacetic acid herbicides such as 4-CPA, 2,4-D, 3,4-DA and MCPA; phenoxybutyric herbicides such as 4-CPB, 2,4-DB, 3,4-DB and MCPB; phenoxypropionic herbicides such as cloprop, 4-CPP, dichlorprop, 3,4-DP, fenoprop, mecopropand mecoprop-P. Preferred herbicidal auxinic carboxylic acids are 2,4-D, triclopyr, aminopyralid, clopyralid, fluoroxypyr, picloram and dicamba.

Choline hydroxide refers to the compound of the formula

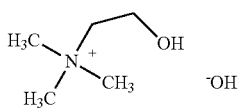

Choline salts of herbicidal auxinic carboxylic acids refers to compounds of the following general formula

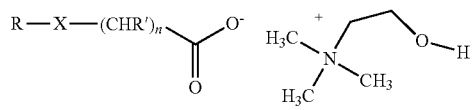

wherein R is a substituted phenyl, pyridinyl, pyrimidinyl, or quinolinyl group, X is O or a single bond, R' is H or $CH_3$ and n is 0 to 3.

The present invention concerns aqueous concentrates comprised of one or more herbicidal auxinic carboxylic acid choline salts that have reduced eye irritancy compared to the commonly used aqueous concentrates of ammonium salts of herbicidal auxinic carboxylic acids. The choline salts have herbicidal activity on an acid equivalent basis comparable to the commercially used carboxylic acid herbicide ammonium salts, but with reduced eye irritation. Furthermore, the choline salts can be conveniently formulated as aqueous concentrates.

The compounds of the present invention can be conveniently prepared by reaction of the herbicidal auxinic carboxylic acid with enough choline hydroxide to fully neutralize the herbicidal auxinic carboxylic acid. The herbicidal auxinic carboxylic acid is mixed with the choline hydroxide in water, optionally with the aid of a co-solvent, to provide the desired aqueous concentrate.

Another aspect of the present invention concerns a mixture of one or more organophosphorous acid herbicide salts and the herbicidal auxinic carboxylic acid choline salts to provide aqueous herbicide concentrates of reduced eye irritancy. The organophosphorous acid herbicides may comprise glufosinate and glyphosate in their commonly used salt forms selected from, for example, ammonium, isopropyl ammonium, dimethyl ammonium, triethyl ammonium, trimethylsulfonium, sodium, potassium and the like. These aqueous concentrate mixtures exhibit reduced eye irritancy compared to mixtures containing herbicidal auxinic carboxylic acid ammonium salts.

Another aspect of the present invention concerns a method of improving the solubility in water of ammonium salts of auxinic herbicides which comprises using the N,N,N-trimethylethanolammonium cation (choline) as the ammonium salt of the auxinic herbicide. Surprisingly, it has been found that for example the triclopyr choline salt has significantly higher solubility in water than any known triclopyr salt even at temperatures as low as about −10° C. For example, the solubility in water of the triclopyr choline salt is greater than the solubility in water of the commercially used triclopyr triethylammonium salt on an acid equivalent or an active ingredient basis. The unexpected high water solubility of the triclopyr choline salt allows the production of higher concentration formulations. High strength formulations are desirable for a variety of economic and environmental reasons. For example, it is desirable to provide a high strength formulation to reduce shipping and handling costs and to reduce the amount of packaging that must be disposed.

The aqueous concentrates of the present invention can generally be employed to control undesirable vegetation in many crops that have been made tolerant to or resistant to them or to other herbicides by genetic manipulation or by mutation and selection. Many glyphosate and glufosinate tolerant crops can be treated as well, alone or in combination with these compounds. Some crops (e.g. corn, soybean and cotton) have been made tolerant to auxinic herbicides such as 2,4-dichlorophenoxyacetic acid. These active ingredients may be used to treat such resistant crops or other auxin tolerant crops.

While it is possible to utilize the aqueous concentrates directly as herbicides, it is preferable to use them in mixtures containing a herbicidally effective amount of the aqueous concentrates along with at least one agriculturally acceptable adjuvant or carrier. Suitable adjuvants or carriers should not be phytotoxic to valuable crops, particularly at the concentrations employed in applying the compositions for selective weed control in the presence of crops, and should not react chemically with the aqueous concentrates or other composition ingredients. Such mixtures can be designed for application directly to weeds or their locus or can be concentrates or formulations that are normally diluted with additional carriers and adjuvants before application.

It is usually desirable to incorporate one or more surface-active agents into the aqueous concentrates of the present invention. The surface-active agents can be anionic, cationic or nonionic in character and can be employed as emulsifying agents, wetting agents, suspending agents, or for other purposes. Typical surface-active agents include salts of alkyl sulfates, such as diethanolammonium lauryl sulfate; alkylarylsulfonate salts, such as calcium dodecylbenzenesulfonate; alkylphenol-alkylene oxide addition products, such as nonylphenol-$C_{18}$ ethoxylate; alcohol-alkylene oxide addition products, such as tridecyl alcohol-$C_{16}$ ethoxylate; soaps, such as sodium stearate; alkylnaphthalenesulfonate salts, such as sodium dibutylnaphthalenesulfonate; dialkyl esters of sulfosuccinate salts, such as sodium di(2-ethylhexyl) sulfosuccinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; and salts of mono and dialkyl phosphate esters.

Other adjuvants commonly used in agricultural compositions include compatibilizing agents, antifoam agents, sequestering agents, neutralizing agents and buffers, corrosion inhibitors, dyes, odorants, spreading agents, penetration aids, sticking agents, dispersing agents, thickening agents, freezing point depressants, antimicrobial agents, and the like. The compositions may also contain other compatible components, for example, other herbicides, plant growth regulants, fungicides, insecticides, and the like and can be formulated with liquid fertilizers.

In the concentrates of the present invention, the active ingredient is generally present in a concentration from about 5 to about 90 weight percent, preferably about 20 to about 80 weight percent. Such compositions are typically diluted with water before application. The diluted compositions usually applied to weeds or the locus of weeds generally contain about 0.001 to about 2 weight percent active ingredient and preferably contain about 0.01 to about 1 weight percent.

The present aqueous concentrates, after dilution in water, can be applied to weeds or their locus by the use of conventional ground or aerial sprayers, by addition to irrigation water and by other conventional means known to those skilled in the art.

The following Examples are presented to illustrate the various aspects of this invention and should not be construed as limitations to the claims.

Example 1

Preparation of aqueous concentrates: The herbicidal auxinic carboxylic acid and choline hydroxide (46 wt % in water) are combined in equimolar amounts in water at room temperature and mixed until a solution is formed to give an aqueous concentrate of the choline salt of the herbicidal auxinic carboxylic acid. Additional inert ingredients may be added to the samples as is well known to those skilled in the art.

Example 2

Eye irritation testing was done according to guideline testing requirements specified in: (1) OECD Guideline for the Testing of Chemicals, Procedure 405 (2002), (2) U.S. EPA Health Effects Test Guidelines, OPPTS 870.2400 (1998), (3) JMAFF 12—Nouan-1847 (2000) and (4) Official Journal of the European Communities, Methods for the Determination of Toxicity, Part B.5 (Eye Irritation), Directive 2004/73/ED, 29 Apr. 2004.

Test material formulations were administered to New Zealand albino rabbit (3 animals per formulation) to determine the potential to produce eye irritation. The material was applied in a single dose to the conjuctival sac of one eye of each animal. The other eye remained untreated and served as a control. Irritation of the cornea, iris and conjunctivae were evaluated 21 days after application of the test material. Maximum irritation scores to be obtained are 4 for corneal opacity, 2 for iritis and 10 for conjunctivitis (these values do not take into account the area of cornea evaluated or additional factors used in the calculations).

The results are reported as irritation present in the cornea, iris and conjunctivae in the most sensitive animal 21 days after application. Testing was conducted with the following nine aqueous concentrates: (1) 2,4-D choline salt (456 grams acid equivalent per liter (gae/l)), (2) 2,4-D Choline salt (538.5 gae/l), (3) 2,4-D DMA (dimethyl ammonium salt, 456 gae/l), (4) 2,4-D DMA (683 gae/l), (5) 2,4-D DMEA (dimethylethanol ammonium, 456 gae/l), (6) 2,4-D IPA (isopropyl ammonium, 456 gae/l), (7) 2,4-D TIPA (triisopropanol ammonium, 456 gae/l), (8) 2,4-D choline (228 gae/l) mixed with glyphosate DMA (dimethyl ammonium, 240 gae/l) and (9) 2,4-D DMEA (228 gae/l) mixed with glyphosate DMA (240 gae/l). As shown in Table 1, 2,4-D choline (sample 1 and 2) and 2,4-D choline mixed with glyphosate DMA (sample 8) had the least amount of irritation present 21 days after application compared to the other 2,4-D amine formulations. 2,4-D choline mixed with glyphosate DMA (sample 8) had no irritation present after 21 days, and 2,4-D choline alone had no or minimal conjunctivitis after 21 days (score of 1). The other 2,4-D amine formulations had corneal opacity ranging from 1-4, iritis ranging from 0-2 and conjunctivitis ranging from 1-6 after 21 days.

TABLE 1

Eye Irritation Scores for 2,4-D Formulations 21 Days After Application of the Test Material

| Sample | Composition of Aqueous Concentrate | 2,4-D gae/L[1] | Cornea | Iris | Conjunctivae |
|---|---|---|---|---|---|
| 1 | 2,4-D choline | 456 | 0 | 0 | 1 |
| 2 | 2,4-D choline | 538.5 | 0 | 0 | 0 |
| 3 | 2,4-D DMA | 456 | 3 | 1 | 3 |
| 4 | 2,4-D DMA | 683 | 4 | 0 | 4 |
| 5 | 2,4-D DMEA | 456 | 4 | 2 | 6 |
| 6 | 2,4-D IPA | 456 | 4 | 0 | 6 |
| 7 | 2,4-D TIPA | 456 | 3 | 0 | 1 |
| 8 | 2,4-D choline + glyphosate DMA[2] | 228 | 0 | 0 | 0 |
| 9 | 2,4-D DMEA + glyphosate DMA[2] | 228 | 1 | 1 | 3 |

[1]grams acid equivalent per liter
[2]glyphosate DMA concentration of 240 gae/L

Example 3

Preparation of aqueous concentrate: A triclopyr choline salt was prepared by reacting triclopyr acid with choline hydroxide in equimolar amounts in water at room temperature. Additional inert ingredients were added to prepare a concentrate containing 360 g/l triclopyr acid equivalent in the form of the choline salt (Sample 10). The composition and amount of the inert ingredients in the Sample 10 formulation were identical to the composition and amount of the inert ingredients in the commercial Garlon® 3A Herbicide containing 360 g/l triclopyr acid equivalent in the form of the triethyl ammonium salt (Sample 11).

Example 4

Eye irritation testing was done according to guideline testing requirements as described in Example 2. Test material formulations were administered to New Zealand albino rabbit (3 animals per formulation) to determine the potential to produce eye irritation as described in Example 2.

The results are reported as irritation present in the cornea, iris and conjunctivae in the most sensitive animal 14 days after application. Testing was conducted with the following two aqueous concentrates: triclopyr choline and triclopyr TEA (triethylamine). As demonstrated in Table 2, no eye irritation was present after 14 days with administration of triclopyr choline (Sample 10), whereas there was presence of corneal opacity (score of 1), and conjunctivitis (score of 1) after 14 days with administration of triclopy TEA (Sample 11).

TABLE 2

Eye Irritation Scores for Triclopyr Formulations 14 Days After Application of the Test Material

| Sample | Composition of Aqueous Concentrate | Triclopyr gae/L[1] | Cornea | Iris | Conjunctivae |
|---|---|---|---|---|---|
| 10 | Triclopyr choline | 360 | 0 | 0 | 0 |
| 11 | Triclopyr TEA | 360 | 1 | 0 | 1 |

[1]grams acid equivalent per liter

Example 5

A triclopyr choline salt solution prepared by reacting 98.7 g triclopyr acid technical (98% purity) with 100.0 g choline hydroxide solution (45%) resulted in a triclopyr choline salt concentration of 68.3% (48.7% triclopyr acid equivalent). The clear, homogeneous solution did not show any crystallization even when stored at −10° C. for 14 days. The solubility of a variety of triclopyr salts in water at 20° C. and 0° C. is reported in Table 3.

TABLE 3

Solubility of Triclopyr Salts in Water at 20° C. and 0° C.

| Triclopyr salt of: | 20° C. | | 0° C. | |
|---|---|---|---|---|
| | wt % AE[1] | wt % AI[2] | wt % AE[1] | wt % AI[2] |
| Dimethylamine | 38.9 | 45.7 | 26.1 | 30.7 |
| Triethylamine | 36.8 | 51.3 | 36.3 | 50.6 |
| Diethanolamine | 13.2 | 18.6 | 5.8 | 8.2 |
| Triethanolamine | 27.4 | 43.3 | 14.2 | 22.5 |
| N,N-dimethylethanolamine | 36.7 | 49.5 | 36.7 | 49.5 |
| Choline | >48.7 | >68.3 | >48.7 | >68.3 |

[1]Acid equivalent (AE) basis as analyzed
[2]Active ingredient (AI) basis as calculated from analyzed value assuming 1:1 molar neutralization Example 6

The cold temperature stability of Sample 1 (456 gae/l 2,4-D choline salt) was compared to the cold temperature stability of Sample 3 (456 gae/l 2,4-D DMA salt). Whereas Sample 3 was solid at a temperature of −10° C., Sample 1 remained a homogeneous, clear liquid at temperatures as low as −20° C., indicating greatly improved solubility at low temperatures.

What is claimed is:

1. A method to reduce the eye irritancy caused by exposure to aqueous herbicidal concentrates of commonly used ammonium salts of auxinic carboxylic acids derived from mono-, di- or trialkylamines, comprising preparing aqueous herbicidal concentrates that include N,N,N-trimethylethanolammonium cations as the ammonium salt of auxinic carboxylic acids selected from benzoic acid herbicides, pyridine carboxylic acid herbicides, pyridinyloxyacetic acid herbicides, phenoxyacetic acid herbicides, phenoxybutyric herbicides, and phenoxypropionic herbicides, wherein the aqueous herbicidal concentrates containing N,N,N-trimethylethanolammonium cations provide reduced eye irritation compared to the commonly used ammonium salts of auxinic carboxylic acids.

2. The method of claim 1 in which the auxinic carboxylic acid is 2,4-D, triclopyr, aminopyralid, clopyralid, fluoroxypyr, picloram or dicamba.

3. The method of claim 1 further including a herbicide salt of glyphosate or glufosinate in admixture with N,N,N-trimethylethanolammonium salt of the auxinic carboxylic acid.

4. The method of claim 1 in which the auxinic carboxylic acid is 2,4-D.

5. The method of claim 3 in which the auxinic carboxylic acid is 2,4-D.

6. The method of claim 3 in which the herbicide salt is glyphosate and the auxinic carboxylic acid is 2,4-D.

7. The method of claim 3 in which the herbicide salt is glufosinate and the auxinic carboxylic acid is 2,4-D.

* * * * *